United States Patent [19]
Wiedner

[11] Patent Number: 5,257,050
[45] Date of Patent: Oct. 26, 1993

[54] GOGGLES, ESPECIALLY PROTECTIVE GOGGLES FOR WORKERS

[75] Inventor: Klaus Wiedner, Fürth/Bay, Fed. Rep. of Germany

[73] Assignee: Uvex Winter Optik GmbH, Fed. Rep. of Germany

[21] Appl. No.: 814,709

[22] Filed: Dec. 30, 1991

[30] Foreign Application Priority Data

Jun. 1, 1991 [DE] Fed. Rep. of Germany ....... 4118018

[51] Int. Cl.[5] ............................ G02C 1/00; G02C 5/12
[52] U.S. Cl. ........................................ 351/86; 351/85; 351/138
[58] Field of Search ................... 351/80, 88, 132, 138, 351/86, 137, 154, 85; 2/446

[56] References Cited
U.S. PATENT DOCUMENTS

| | | | |
|---|---|---|---|
| 3,384,903 | 5/1968 | Malcom | 351/44 |
| 4,405,214 | 9/1983 | Bolle . | |
| 4,759,622 | 7/1988 | Schmidthaler . | |
| 4,799,781 | 1/1989 | Weber . | |

FOREIGN PATENT DOCUMENTS 2419526  11/1979  France ............................ 351/138

Primary Examiner—Rodney B. Bovernick
Attorney, Agent, or Firm—Laff, Whitesel, Conte & Saret

[57] ABSTRACT

For a pair of goggles, in particular protective goggles for worker, it is provided for the exchangeable fixing of the sight pieces, which however meets also the working protection conditions, that the sight pieces are fixed each laterally at undercuts of the frame and are fixed in the vicinity of the nose rib by pushing on a holder. The holder embraces the nose rib region in a flat manner and is lockable at the upper side of the frame, so that an inadvertent releasing of the sight pieces is prevented.

5 Claims, 2 Drawing Sheets

GOGGLES, ESPECIALLY PROTECTIVE GOGGLES FOR WORKERS

FIELD OF THE INVENTION

The present invention relates to a pair of goggles, especially protective goggles for workers, with a frame, which surrounds two sight pieces, a nose rib being formed at the frame between the two sight pieces, and a holder being placeable onto the nose rib.

BACKGROUND OF THE INVENTION

Goggles of this species are used as protective goggles, in particular in sports. In the field of work protection goggles are known with only one single continuous sight piece being provided, which is inserted into a frame which is injection-molded in one piece. Accordingly with these goggles the finished goggles are simply constructed with a large field of vision, however, cannot be adapted individually to the specific anatomic conditions of the respective user. Furthermore the sight piece cannot be exchanged, so that for example a special adaptation of the sight pieces to the respective purpose of application, for instance by selecting a corresponding darkening, is not possible. In addition, sight pieces which are clouded by grinding dust or the like could not be exchanged.

SUMMARY OF THE INVENTION

With the above considerations in mind, it is the object of the invention to provide a pair of protective goggles for workers which ensures a high degree of individual adaptability not only to the anatomy of the user, but also to the respective purpose of application, which, however, guarantees nevertheless a high protective effect.

This object is attained in accordance with the invention by fixing the sight pieces each laterally at undercuts of the frames and by fixing them by pushing on the holder in the vicinity of the nose rib.

Numerous constructions per se have already become known, in which the sight pieces are held laterally at the frame by hooks or protrusions or similar measures and are held in the nose region by a releasable locking mechanism.

These known glasses, however, refer essentially to fashionable glasses, in particular sun glasses, and less to goggles for which the protective effect is important. The embodiment according to the invention ensures also for protective goggles for workers that such a firm attachment of the sight pieces is attained, so that these meet for example the required shot test stability.

In addition an advantageous further embodiment according to the invention is not known from the conventional glasses, which embodiment provides that the holder has nose pads on its underside and correspondingly serves simultaneously as a carrier for nose pads and is pushed on from the underside.

Accordingly, the holder accomplishes a double function as a carrier for the nose pads and as a locking part for the sight pieces. The conventional locking mechanisms were formed as separated parts respectively and have caused accordingly additional constructive expenditure.

Furthermore it is preferably provided that the holder with a rib section fits over the inner rims of the sight pieces in the vicinity of the nose rib and fixes them against the nose rib. By means of that not only a fixing of the sight pieces along a larger section of their outer rim is attained, but also a very attractive design is realized.

It is furthermore provided advantageous that at the upper side of the holder a locking protrusion is disposed, which can be locked into a corresponding locking recess at the upper side of the frame with an axial fixing. This effect ensures that the holder is fixed reliably after having reached its end position, which also contributes essentially to a safe fixing of the sight pieces for work protection applications.

According to a further advantageous embodiment of the invention the sight pieces have appendages at their upper side which rearwardly extend approximately rectangularly outward from the plane of the sight pieces, and which fit over the upper side of the frame in the inserted position. By means of that on the one hand a safe protection of the region at the upper side of the frame against the penetration of light and foreign substances is attained, and on the other hand the sight pieces are fixed in the downwards direction in this manner. Finally a very smooth line guidance is thus attained which leads to an attractive design.

In this meaning it can further be provided that the appendages at the sight pieces in the nose rib region are in alignment with a frame part provided in this region at the frame and accommodating the locking device, so that with inserted sight pieces a continuous upper side of the goggles is provided.

Ensuing the invention is described in terms of a preferred embodiment taken in conjunction with the drawing.

DESCRIPTION OF THE PREFERRED EMBODIMENTS

Figure 1:
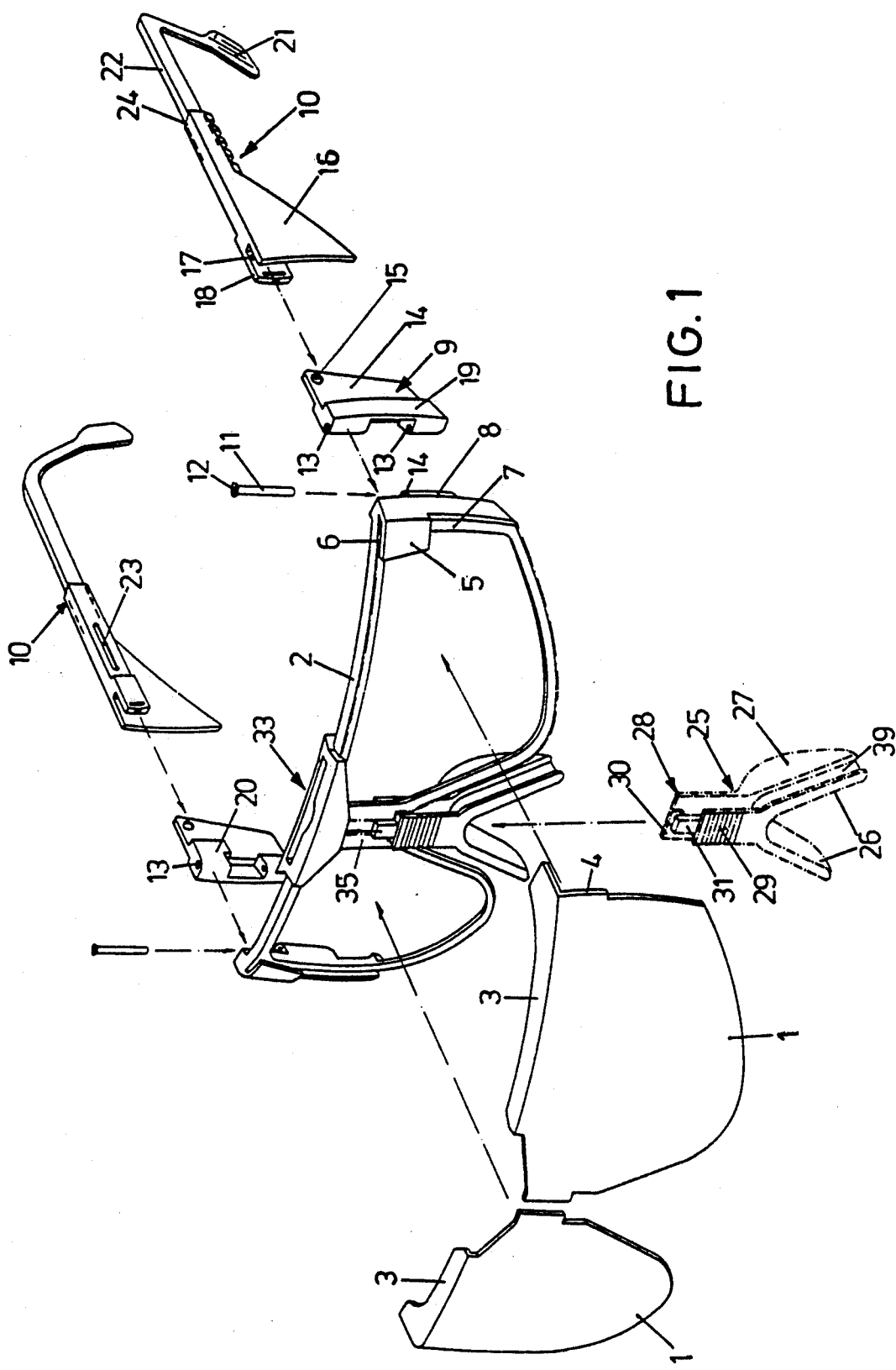
FIG. 1 shows a perspective explosive illustration of a pair of goggles according to the invention.
Figures 2, 3:
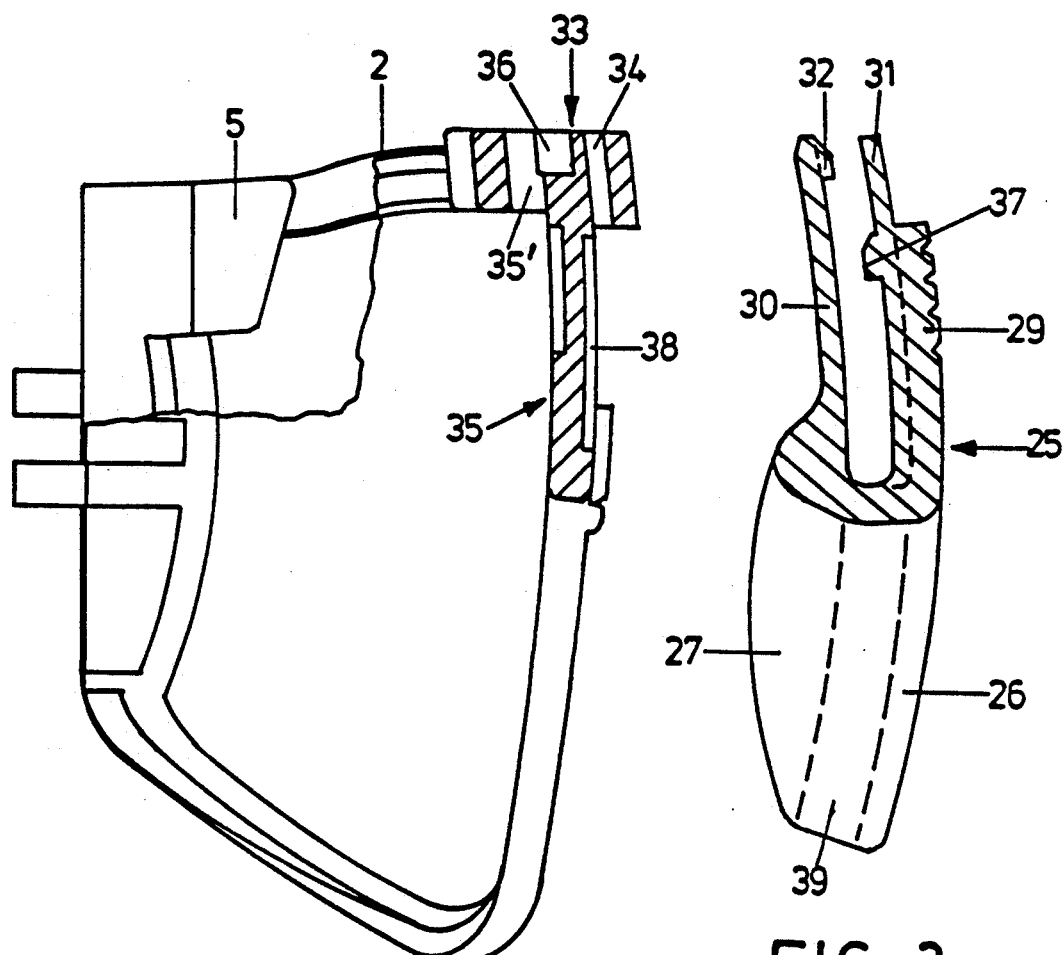
FIG. 2 shows a section taken through the nose rib region and FIG. 3 shows a section taken through the holder which is to be placed on the nose rib region.

A pair of goggles shown in the drawing comprises two sight pieces 1 and a frame 2 injection molded in one piece from plastics material.

At the upper side of the sight pieces 1 an appendage 3 is provided respectively, which extends towards the face of the user horizontally outwards of the plane of the sight pieces 1, the inner rim of each appendage 3 being anatomically adapted to the face form of the user.

Below the appendages 3 the sight pieces 1 have lateral protrusions 4 in the extension of the plane of the sight pieces, which protrusions 4 are placed in an undercut 6 behind the appendages 5 of the frame 2, when the sight pieces 1 are placed from above onto the frame 2.

At the back side of the appendages 5 hinge eyes 8 are provided at the frame section 7, which is vertical in the position of use, onto which hinge eyes 8 a bearing part 9 for a temple 10 can be placed embracing the hinge appendages 8, and a hinge bearing bolt 11 with a thickened upper end 12 can be inserted through the hinge bores 13 of the bearing part 9 in a per se known manner, the bolt 11 simultaneously passing through a bore 14 in the hinge appendage 8.

Adjoining the hinge range the bearing part 9 has a plate 14, which has a bearing bore 15 at its rear upper end.

The temples 10 have a lateral protection plate 16 and at its inner side a bearing pin 17, which can be locked into the bearing bore 15, an appendage 18 extending parallel to the bearing plate 16 ensuring with a per se known inclination locking that the plate appendage 9 is placed fork-shaped between the plate 16 and the appendage 18 of the temple 10. The outer side of the protection plate 16 is in alignment with the outer side 19 of the hinge bearing part 9 and the outer side of the appendage 18 is in alignment with the inner side 20 of the hinge bearing part 9.

An ear part 21 of the temple 10 has a linear section 22 with at least one locking protrusion not shown in the drawing, which interacts with locking recesses, which are neither shown in detail, in a lateral slot 23, when putting the section 22 into a recess 24 of the temple 10 for the length adjustment of the ear part 21.

A holder 25 shown in the drawing in the middle below in dashed lines and in the middle on top in solid lines and shown in the placed-on position, has two appendages 26, which are disposed approximately V-shaped, and at which back sides nose pads are disposed.

At the upper side of the appendages 26 an approximately U-shaped locking part 28 is provided, which comprises a front plate 29 and a rear plate 30. When pushing the holder 25 onto the frame 2, the front plate 29 fits over the front side of the inserted sight pieces 1 and the rear plate 30 fits over the rear side of the nose rib 35.

A guide pin 31 is disposed at the upper side of the front plate 29 and a locking protrusion 32 is disposed at the inner side of the rear plate 30, and in a locking part 33 secured at the upper side of the frame 2 a guide recess 34 for the guide appendage 31 and a guide recess 35 for the plate 30 are formed. The guide recess 35' has an undercut 36, into which the locking protrusion 32 locks precisely, so that it is absolutely ensured that the sight pieces 1 cannot be released inadvertently, but that the holder 25 can be removed for exchanging the sight pieces only if the locking protrusion 32 is disengaged manually.

A protrusion 37 at the inner side of the plate 29 engages with a corresponding recess 38 at the front side of the locking part 33 and thus ensures also a precise guidance and fixing.

The appendages 26 accommodating the nose pads 27 have grooves 39, which embrace the outer rim at the underside of the frame 2 and of the sight pieces 1 and thus ensure an additional fixing in this manner.

What is claimed is:

1. A pair of goggles, in particular protective goggles, with a frame, which accommodates two sight pieces, a bridge-like nose rib being formed on the frame between the two sight pieces, and a holder being placeable onto the nose rib, and the sight pieces being laterally fixed on undercuts of the frame and cooperating with the holder in a vicinity of the nose rib, said sight pieces having appendages extending at their upper side rearwardly from a plane of the sight pieces, said appendages fitting over an upper side of the frame, in the inserted position, a locking part arranged on the upper side of the frame, said sight pieces being fixed by said frame by said locking part and said holder.

2. A pair of goggles according to claim 1, wherein the holder (25) has nose pads (27) at its underside.

3. A pair of goggles according to claim 1, wherein the holder (25) with a rib section (plates 29, 30) fits over the inner rims of the sight pieces (1) in the vicinity of the nose rib (35).

4. A pair of goggles according to claim 1, wherein the holder (25) has grooves (39) in the vicinity of the nose pads (27), which fit over the outer rim of the frame (2) below the nose rib (35) in the placed-on position and additionally fix the rim of the sight pieces (1).

5. A pair of goggles in particular protective goggles with a frame which accommodates two sight pieces comprising a nose rib being formed on the frame between the two sight pieces, a holder being placeable on to the nose rib, the sight pieces being each laterally fixed on undercuts of the frame and cooperate with the holder in a vicinity of nose rib by pushing on the holder, the sight pieces having appendages at their upper side, said appendages rearwardly extending approximately rectangularly outward from a plane of the sight pieces and which fit over the upper side of the frame in an inserted position, and said appendages at the sight pieces in the nose rib region are in alignment with a locking part, which is provided in the nose rib region and which accommodates a locking device.

* * * * *